United States Patent [19]

Thompson

[11] Patent Number: 5,758,659
[45] Date of Patent: Jun. 2, 1998

[54] WOUND TAB CONDOM AND METHOD OF APPLICATION

[76] Inventor: Robert B. Thompson, 10503 SW. 153 St., Miami, Fla. 33157

[21] Appl. No.: 824,432

[22] Filed: Mar. 26, 1997

[51] Int. Cl.$^6$ .................................................. A61F 6/04
[52] U.S. Cl. .................................. 128/844; 128/918
[58] Field of Search .......................... 128/842, 844, 128/918; 604/347–353

[56] References Cited

U.S. PATENT DOCUMENTS

| | | | |
|---|---|---|---|
| 4,949,731 | 8/1990 | Harding | 128/842 |
| 5,314,447 | 5/1994 | Papurt | 128/844 |
| 5,531,230 | 7/1996 | Bell | 128/844 |
| 5,651,374 | 7/1997 | Wester | 128/844 |

FOREIGN PATENT DOCUMENTS 9008522   8/1990   WIPO ................................ 128/918

*Primary Examiner*—Michael A. Brown
*Attorney, Agent, or Firm*—Robert J. Van Der Wall

[57] ABSTRACT

A condom includes a condom tubular side wall having a first side wall end and a second side wall end, the tubular side wall being rolled outwardly and over itself from the second side wall end toward the first side wall end to form a side wall roll; a condom end wall sealingly joined to the tubular side wall at the first side wall end; and at least one strip of flexible material having a gripping tab end segment with a touch distinctive tactile surface on one side thereof, the at least one strip being wound within the side wall roll so that the gripping tab end segment and touch distinctive tactile surface of the at least one strip protrudes from the side wall roll. A method of assembling the condom includes the step of winding the at least one strip together with the tubular side wall outwardly and over the tubular side wall toward the side wall second end to form a side wall roll, so that the gripping tab end segment protrudes from the side wall roll. A method of applying the condom to a penis includes the steps of grasping the tab end segment, touching the touch distinctive tactile surface thereon, orienting the condom so that the tubular side wall roll is directed away from the user, placing the condom end wall against the distal end of the penis, and pulling the tab end segment laterally outwardly from the tubular side wall, so that the side wall roll unrolls over and advances longitudinally along the penis.

7 Claims, 2 Drawing Sheets

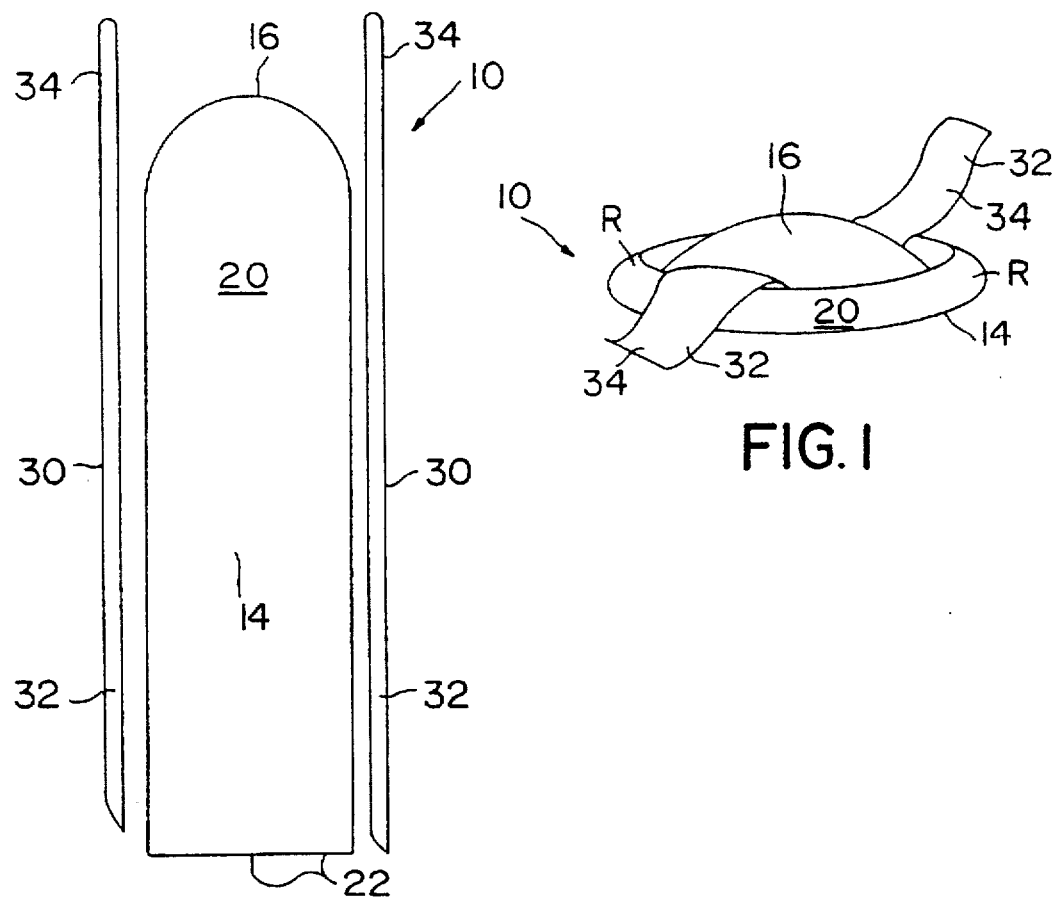
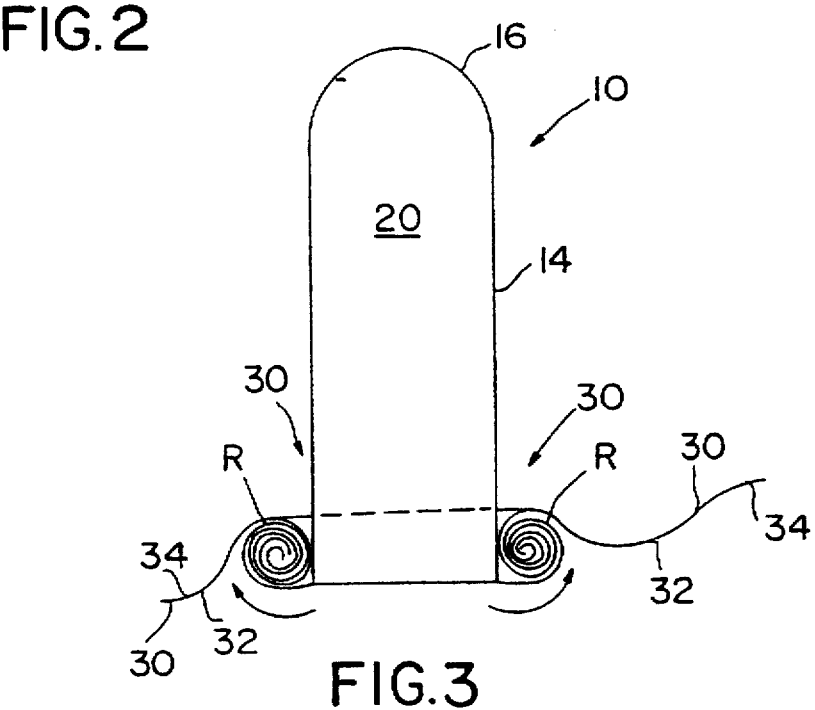

WOUND TAB CONDOM AND METHOD OF APPLICATION

BACKGROUND OF THE INVENTION

1. Field of the Invention

The present invention relates generally to the field of birth control and sexually transmitted disease prevention devices. More specifically the present invention relates to a condom with an integrated condom applicator assembly.

The condom itself is of generally conventional design, having a condom tubular side wall, a closed end with an end wall and an open end with a side wall rim. The condom is provided with the tubular side wall wound outwardly and over itself from the side wall rim toward the end wall to form a side wall roll.

The inventive condom applicator assembly is formed of two strips of flexible material, wound with the tubular side wall into the side wall roll such that the tab end segments protrude from the roll. The end tab segments are preferably provided with a tactile surface on one side thereof so that a user can orient the side wall roll in the proper direction in the dark. The term tactile surface refers to a surface on one side of the end tab segments which can be distinguished from the normal surface by the sense of touch, such as a roughened surface. A method of condom assembly is provided in which the strips are wound into the side wall roll.

To use the condom, the user places the condom end wall against the distal end of the penis, so that the side wall roll is directed away from the user. This is accomplished in the dark by the user's sense of touch of the optional tactile surfaces when the user grasps the two tab end segments. The user then pulls the two tab end segments laterally outward from the sides of the penis. This single action causes the side wall roll to rapidly unwind around and longitudinally along the penis.

2. Description of the prior Art

There have long been various types of condoms and condom packages. Condoms have included lubricated and unlubricated versions and have been made of various materials, such as latex. Condom packages have included sealed envelopes, wrappers and flat metal containers. A problem with these prior condoms and condom packages has been that they do not assist the user in condom application, and application is difficult in the dark because the user cannot see which way to orient the condom.

It is thus an object of the present invention to provide a condom including an integral applicator assembly.

It is another object of the present invention to provide such a condom in which the applicator assembly does not significantly The term tactile surface refers to a surface on one side of the end tab segments which can be distinguished from the normal surface by the sense of touch, such as a roughened surface increase the size of the condom a touch distinctive surface.

It is a further object of the invention to provide a means for orienting the condom so that the applicator can be reliably and easily operated by touch in the dark. This is accomplished by having one side of end tab segments provided with a touch distinctive surface.

It is still another object of the present invention to provide such a condom in which the applicator assembly causes the condom to unroll rapidly over the penis with a single movement of the user's hands.

It is finally an object of the present invention to provide such a condom in which the applicator assembly is inexpensive to manufacture.

SUMMARY OF THE INVENTION

The present invention accomplishes the above-stated objectives, as well as others, as may be determined by a fair reading and interpretation of the entire specification.

A condom is provided including a condom tubular side wall having a first side wall end and a second side wall end, the tubular side wall being rolled outwardly and over itself from the second side wall end toward the first side wall end to form a side wall roll; a condom end wall sealingly joined to the tubular side wall at the first side wall end; and at least one strip of flexible material having a gripping tab end segment with a tactile surface on one side thereof, the at least one strip being wound within the side wall roll so that the gripping tab end segment of the at least one strip protrudes from the side wall roll such the gripping tab end segment can be easily grasped and the touch distinctive tactile surface felt.

The condom preferably includes at least two of the strips of flexible material wound within the side wall roll, the two strips being positioned on laterally opposing portions of the tubular side wall. The condom preferably is formed of latex condom material, and the at least one strip preferably is formed of the latex condom material. The at least one strip preferably is of sufficient length to extend at least from the side wall second end to the side wall first end. Touch distinctive tactile are preferably provided at least on the gripping tab end segment thereof.

A method is provided of assembling the condom, including the step of winding the at least one strip together with the tubular side wall outwardly and over the tubular side wall toward the side wall first end to form a side wall roll, so that the gripping tab end segment and touch distinctive tactile surface protrude from the side wall roll.

A method is provided of applying the condom to a penis, including the steps of grasping the tab end segment, feeling the tactile surface thereon, orienting the condom in the proper direction, placing the condom end wall against the distal end of the penis, so that the tubular side wall roll is directed away from the user; and pulling the tab end segment laterally outwardly from the tubular side wall, so that the side wall roll unrolls over and advances longitudinally along the penis. The method preferably includes the additional step of lifting the at least one strip away from the tubular side wall.

BRIEF DESCRIPTION OF THE DRAWINGS

Various other objects, advantages, and features of the invention will become apparent to those skilled in the art from the following discussion taken in conjunction with the following drawings, in which:

FIG. 1 is a perspective view of the condom and the condom applicator assembly in its rolled configuration as provided to the user.

FIG. 2 is a side view of the condom body extended to full length prior to winding of the tubular side wall, and of two strips to be wound together with the side wall into a side wall roll as shown in FIG. 1.

FIG. 3 is a cross-sectional side view of the condom body and strips partly assembled, the tubular side wall being partially wound into a side wall roll and the two strips shown in FIG. 2 being wound together with and into the tubular side wall.

DETAILED DESCRIPTION OF THE PREFERRED EMBODIMENTS

Figure 4:
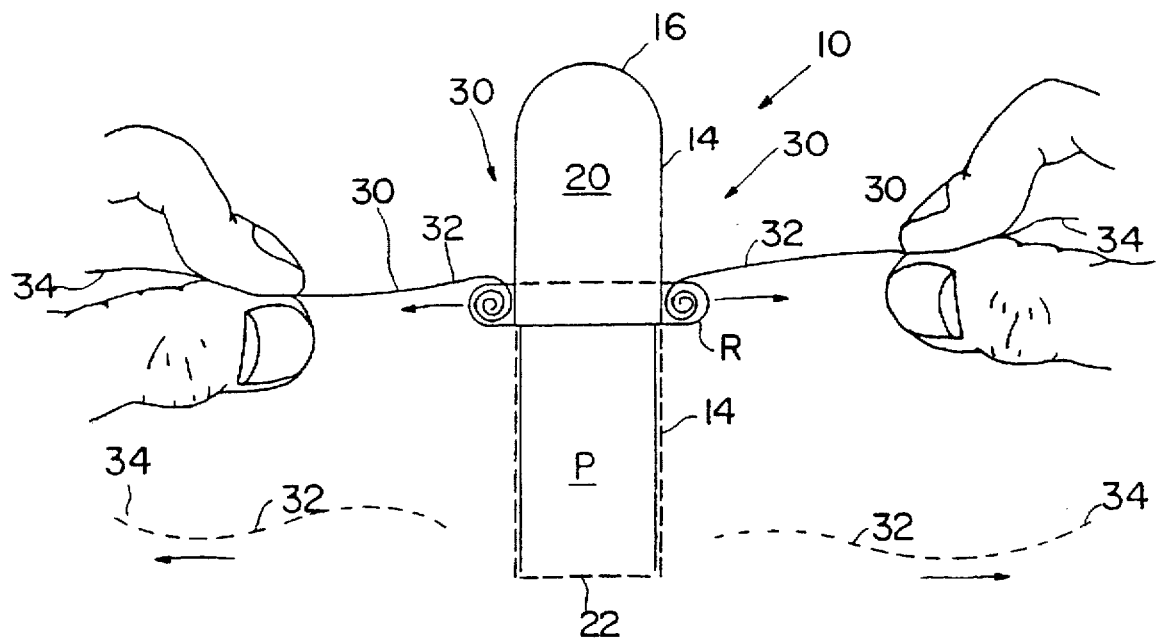
FIG. 4 is a cross-sectional side view as in FIG. 3, except that the roll is shown partially unwound in solid lines as the user's hands advance radially outward from the sides of the penis. The fully unrolled tubular side wall is illustrated in broken lines, with the strips released and separated.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 5:
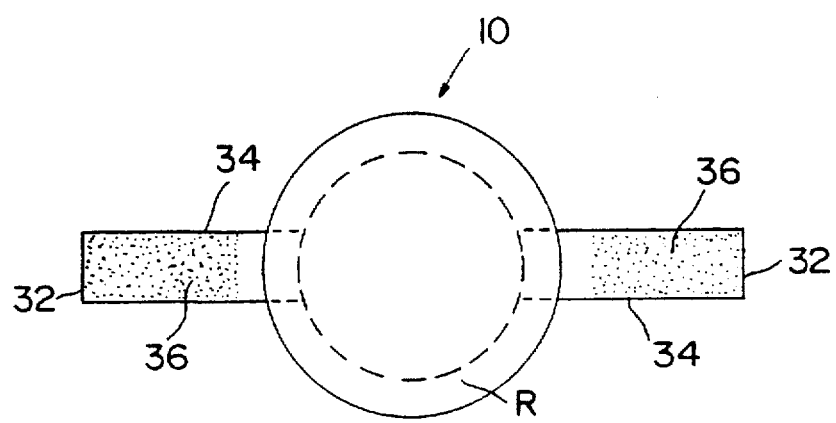
FIG. 5 is a bottom view showing the touch distinctive tactile surfaces on the tab end segments.

Referring to FIGS. 1–5, a condom 10 including a condom body 20 and an integrated condom applicator assembly 30 is disclosed. Condom body 20 is of conventional condom design, having a condom tubular side wall 14, a closed first side wall end with a condom end wall 16 and an open second side wall end with a condom tubular side wall rim 22. Condom 10 is provided to the consumer in the conventional product configuration, i.e., with the tubular side wall 14 wound outwardly and over itself from side wall rim 22 toward end wall 16 to form a side wall roll R.

The inventive condom applicator assembly 30 includes at least one, and preferably two strips 32 of flexible material. The material is preferably condom material. Strips 32 are separate from the main condom body 20 and are wound longitudinally with rolled tubular side wall 14 so that gripping tab end segments 34 of strips 32 protrude from side wall roll R. See FIGS. 1–3. Gripping tab end segments 34 have, on one side, touch distinctive tactile surfaces 36. See FIG. 5.

Method

In practicing the invention, the following method may be used. A method of condom 10 manufacture is provided in which strips 32 are cut from a sheet of flexible material to be of sufficient length to extend at least from the side wall rim 22 to substantially the condom end wall 16. See FIG. 2. Strips 32 are wound together with side wall 14 as side wall 14 is rolled outwardly and over itself in the conventional condom fashion, to an extent that gripping tab end segments 34 with touch distinctive tactile surfaces 36 of strips 32 remain free and protruding from side wall roll R. See FIGS. 3 and 5. Then condom 10 preferably is packaged in a conventional sealed condom 10 container (not shown).

To use condom 10, the user grasps each tab end segment 34 between the thumb and the index finger of the closest hand and touches the tactile surfaces 36 to orient the condom in the proper direction because if it is not properly oriented, it will unwind in the wrong direction. If necessary, the condom is turned over. See FIG. 5. The user then places condom end wall 16 against the distal end of the penis p in the conventional way, so that tubular side wall roll R is directed away from the user. Then the user grasps each tab end segment 34 between the thumb and the index finger of the closest hand and pulls tab end segments 34 radially outward from the sides of the penis p. See FIG. 4. This single action causes the rolled side wall 14 to quickly unwind and advance longitudinally over the penis p. Once tubular side wall 14 is fully unwound, strips 32 are necessarily unwound as well and freed from condom body 20, so that strips 32 may be lifted away from condom body 20 by the user. Strips 32 are later collected and discarded together with the used condom body 20.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A condom, comprising:

a condom tubular side wall having a first side wall end and a second side wall end, said tubular side wall being rolled outwardly and over itself from said second side wall end toward said first side wall end to form a side wall roll;

a condom end wall sealingly joined to said tubular side wall at said first side wall end;

and at least one strip of flexible material having a gripping tab end segment, said at least one strip being wound within said side wall roll such that said gripping tab end segment of said at least one strip protrudes from said side wall roll exposing a touch distinctive tactile surface on one side of said gripping tab end segment.

2. The condom of claim 1, comprising at least two said strips of flexible material wound within said side wall roll, said two strips being positioned on laterally opposing portions of said tubular side wall.

3. The condom of claim 1, wherein said condom is formed of latex condom material, and wherein said at least one strip is formed of said latex condom material.

4. The condom of claim 1, wherein said at least one strip is of sufficient length to extend at least from said side wall second end to said side wall first end.

5. A method of assembling a condom including an applicator assembly, said condom comprising a condom tubular side wall having a first side wall end and a second side wall end and a condom end wall sealingly joined to said tubular side wall at said first side wall end; said condom applicator assembly comprising at least one strip of flexible material having a gripping tab end segment, comprising the step of:

winding said at least one strip together with said tubular side wall outwardly and over said side wall toward said side wall first end to form a side wall roll, such that said gripping tab end segment protrudes from said side wall roll exposing a touch distinctive tactile surface on one side of said gripping tab and segment.

6. A method of applying a condom having a condom applicator assembly to a penis, said condom comprising a condom tubular side wall having a first side wall end and a second side wall end, said tubular side wall being rolled outwardly and over itself from said second side wall end toward said first side wall end to form a side wall roll and a condom end wall sealingly joined to said tubular side wall at said first side wall end; said condom applicator assembly comprising at least one strip of flexible material having a gripping tab end segment having a touch distinctive tactile surface on one side thereof, said at least one strip being wound within said side wall roll such that said gripping tab end segment and tactile surface of said at least one strip protrudes from said side wall roll, comprising the steps of:

grasping said tab end segment;

touching said touch distinctive tactile surface;

orienting said condom such that said tubular side wall roll is directed away from the user;

placing said condom end wall against the distal end of the penis; and pulling said tab end segment laterally outwardly from said tubular side wall, such that said side wall roll unrolls over and advances longitudinally along the penis.

7. The method of claim 6, comprising the additional step of:

lifting said at least one strip away from said tubular side wall.

* * * * *